United States Patent [19]

Rosar et al.

[11] Patent Number: 5,300,068
[45] Date of Patent: Apr. 5, 1994

[54] ELECTROSURGICAL APPARATUS

[75] Inventors: George C. Rosar, Brooklyn Park; Ken W. Bachofer, Brooklyn Center; James L. Pokorney, Shoreview; James E. Graf, New Brighton, all of Minn.

[73] Assignee: St. Jude Medical, Inc., St. Paul, Minn.

[21] Appl. No.: 871,742

[22] Filed: Apr. 21, 1992

[51] Int. Cl.$^5$ .......................... A61B 17/36
[52] U.S. Cl. .......................... 606/34; 606/32
[58] Field of Search .......................... 606/32, 34, 35, 37, 606/38, 39, 40

[56] References Cited

U.S. PATENT DOCUMENTS

| | | | |
|---|---|---|---|
| 3,566,877 | 1/1968 | Smith et al. | 128/422 |
| 4,154,246 | 5/1979 | LeVeen | 128/784 |
| 4,244,371 | 1/1981 | Farin | 606/34 |
| 4,416,276 | 11/1983 | Newton et al. | 606/35 |
| 4,473,075 | 9/1984 | Rexroth | 606/37 |
| 4,550,727 | 11/1985 | Rexroth | 606/37 |
| 4,574,801 | 3/1986 | Manes | 128/303.14 |
| 4,658,819 | 4/1987 | Harris et al. | 128/303.13 |
| 4,658,820 | 4/1987 | Klicek | 606/37 |
| 4,682,596 | 7/1987 | Bales et al. | 128/303.14 |
| 4,727,874 | 3/1988 | Bowers et al. | 606/40 |
| 4,748,986 | 6/1988 | Morrison et al. | 128/772 |
| 4,754,757 | 7/1988 | Feucht | 606/32 |
| 4,945,912 | 7/1990 | Langberg | 128/642 |
| 4,961,739 | 10/1990 | Thompson | 606/37 |
| 5,167,658 | 12/1992 | Ensslin | 606/34 |
| 5,167,660 | 12/1992 | Altendorf | 606/40 |
| 5,190,517 | 3/1993 | Zieve et al. | 606/38 |

FOREIGN PATENT DOCUMENTS

| | | | |
|---|---|---|---|
| WO9007303 | 7/1990 | PCT Int'l Appl. | |
| 2225534 | 6/1990 | United Kingdom | 606/34 |

OTHER PUBLICATIONS

Slager et al, "Spark Erosion And Its Combinaton With Sensing Devices For Ablation Of Vascular Lesions", in Interventional Cardiology, Future Directions, Vogel et al, eds. 1989, 158-169.

Kelly et al,"Electrosurgery", 1932, pp. 14-25.

"Automatic Control Of Length of Welding Arc", NASA Tech Briefs, Nov. 1991, p. 91.

Primary Examiner—William E. Kamm
Assistant Examiner—Samuel Gilbert
Attorney, Agent, or Firm—Leydig, Voit & Mayer

[57] ABSTRACT

An electrosurgical apparatus for cutting tissue and for ablating occlusions includes a pulse generator for selectively generating a train of pulses of electrical energy for application to a wire having an attached electrode, the generator having a variable output impedance, the wire and the electrode being at least part of a load impedance. The apparatus senses the load impedance relative to the output impedance and adjusts the output impedance to match the load impedance. The generator produces pulses of variable energy, measures the relative electrical energy produced by an arc in response to a pulse, compares the relative electrical energy to a predetermined value to determine an energy difference, and adjusts the energy of a subsequent pulse to reduce the energy difference for the subsequent pulse toward zero.

22 Claims, 7 Drawing Sheets

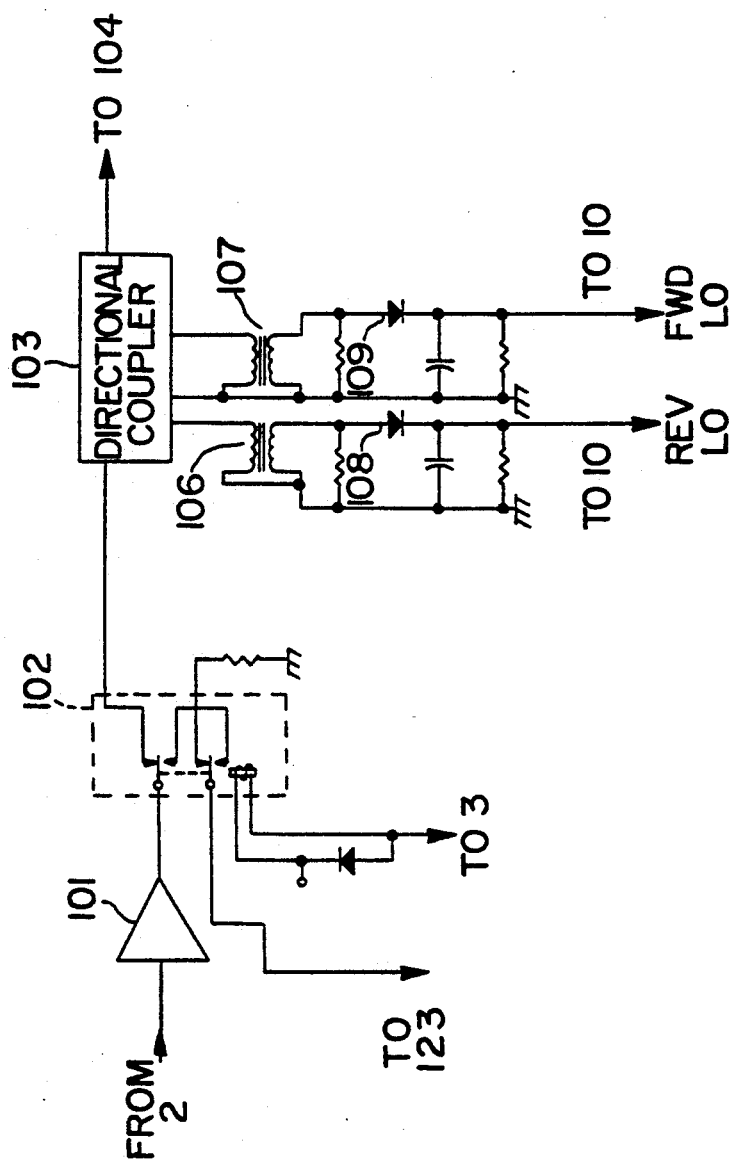

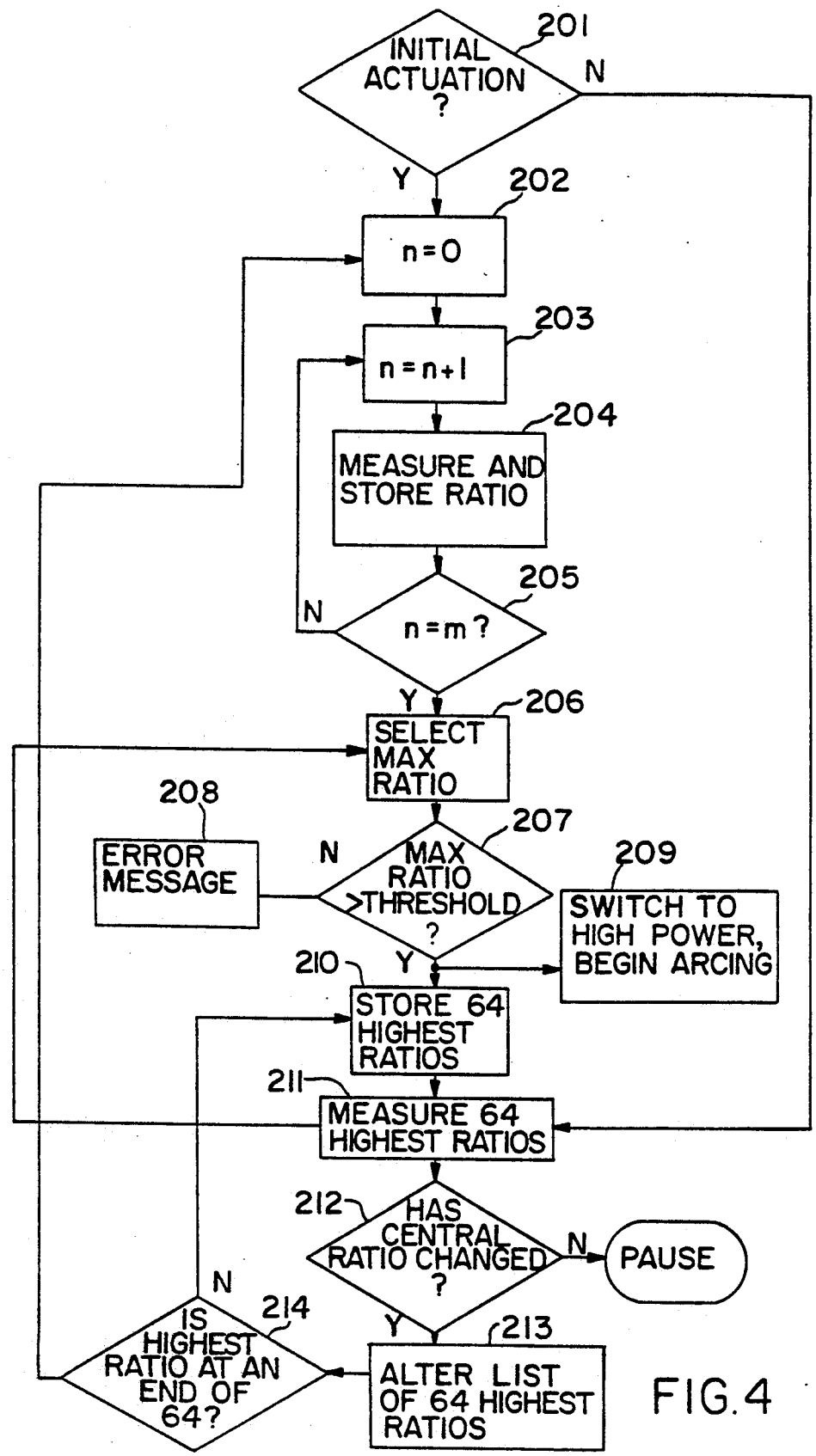

ELECTROSURGICAL APPARATUS

FIELD OF THE INVENTION

The present invention concerns an electrosurgical apparatus for ablating tissue and occlusions, particularly within liquid-filled lumens of animals, such as arteries and vessels of a human, with an electrical arc produced at an electrode. More particularly, the invention concerns an apparatus providing an impedance match between an electrosurgical electrode and its environs and the source of electrical pulses, controllably adjusting the electrical energy of the pulses to produce an arc of desired energy, and a guide wire having an electrode for supporting monopolar arcing, particularly within a lumen.

BACKGROUND OF THE INVENTION

The use of electrical arcing in surgical procedures has been known for some time. In one external application, an electrical scalpel, sometimes referred to as a Bovee knife, is employed to simultaneously make an incision and cauterize the incised tissue. In the use of that apparatus, a surgeon can visually observe the arcing between the knife and tissues and the cutting of the tissue. The surgeon can make adjustments in the position of the scalpel or in the electrical signal for controllably making and cauterizing an incision. For example, if the arc is observed to be too strong, either the electrical energy supplied to the scalpel can be reduced or the scalpel can be moved to a position farther from the tissue.

Electrical ablation of occlusions within lumens, such as arteries and vessels, has also been known for some time. In that technique, a wire, catheter, or other implement, generically referred to here as a wire, having an electrode at its end is inserted into a vessel or artery and moved to a position adjacent an occlusion. Once an occlusion is encountered, electrical energy, usually in the form of pulses, is supplied to the electrode so that arcing occurs. The plaque forming the occlusion is vaporized or reduced to very small particles if the arcing ablation proceeds as intended. In some apparatus, for example, the type described in U.S. Pat. No. 4,682,596 to Bales et al, a bipolar catheter is employed. In a bipolar catheter, two wires are inserted in the lumen and two electrically isolated electrodes are present at the end of the catheter. Arcing occurs between the two electrodes. In other known apparatus, an example of which is described in PCT Application W090/07303 to Janssen, a monopolar, rather than bipolar, catheter may be employed. A monopolar catheter is used in conjunction with a dispersive electrode or ground pad that is placed on a portion of an animal's body, such as a human's belly or thigh, which provides an electrical return path. Arcing then occurs between a single electrode at the end of the catheter and the grounded body. Janssen also discloses a bipolar arcing catheter apparatus.

In addition to occlusion removal, percutaneous electrosurgery may be carried out in other liquid-containing body cavities or lumens where visual observation is difficult or impossible. For example, arthroscopic procedures may be used for releasing or shaping ligaments. In laparoscopic techniques, nerves may be severed, tissues may be incised, and parts or all of organs removed through a relatively small incision that is far less invasive than conventional surgery. Urological surgery, such as transurethral resection of the prostate and ablation of cancerous tissues, also may be carried out using electrosurgical techniques. Vascular ablation has already been extended to plaque ablation within the heart in the presence of blood. In all of these procedures, the cavity or lumen in which the electrosurgery takes place is partially or completely filled with a fluid, such as blood or a saline solution, that affects and usually interferes with the electrosurgery.

There is a significant difference between external electrosurgery, such as the use of the Bovee knife, and other internal vascular electrosurgery, such as occlusion ablation. In internal electrosurgery, it is impossible to observe the arcing causing plaque removal or cutting of tissues. In fact, it is even difficult to determine the position of the electrode where arcing is taking place. Janssen suggests the use of ultrasound to determine the location of the electrode. Other techniques include adding a contrast medium for fluoroscopic observation of the position of the electrode. While these and other techniques may permit determination of the location of an electrode, they do not permit observation or control of arcing to ensure that an arc occurs and has particular qualities.

Producing an arc, particularly a monopolar arc, within a liquid, such as a saline solution or blood, presents difficult problems. For example, the efficiency of the arcing and tissue removal decreases significantly as compared to external electrosurgery. The typical response to this efficiency problem with known electrosurgical apparatus is an increase in the electrical power applied to the electrode. However, increased power may cause damage to patient tissue remote from the surgical site, increasing the risk that the surgeon will receive an electrical shock, raising the probability of undesired tissue charring or excessive incision, and may cause loss of sensitivity in the surgeon's control.

It is well known that the electrical impedance of an electrosurgical electrode and connecting wire varies depending upon the position, i.e., depth of insertion, relative to a body, the quantity of adjacent liquid, if any, and other variable factors. The prior art has not taken into account the varying load impedance as a wire and electrode are advanced in a body cavity or lumen or the effect of the impedance change on the energy of an arc and the resulting surgical process. In an electrosurgical scalpel application, i.e., in a dry environment, it has been recognized that, as moisture is driven from tissue by bipolar arcing, impedance increases and can result in problems such as adhering of instruments to tissue (see, for example, U.S. Pat. No. 4,658,819 to Harris et al).

SUMMARY OF THE INVENTION

It is a general object of the invention to provide an electrosurgical apparatus for cutting tissues and for ablating vascular occlusions by producing controlled arcing.

Another object of the invention is to provide an apparatus for generating a train of pulses of electrical energy supplied to an electrosurgical electrode wherein the output impedance of the source of the pulses is continually matched to the load impedance presented by the electrosurgical electrode and its environs.

Another object of the invention is to provide an apparatus for generating a train of pulses of electrical energy supplied to an electrosurgical electrode in which the energy of an arc at the electrosurgical electrode produced by a pulse is monitored and the energy of subsequent pulses is adjusted in response to the monitored energy to adjust the arc energy toward a predetermined value.

It is yet another object of the invention to provide a guide wire including an electrically insulated wire, an electrically and thermally insulating tip mounted on an end of the wire that extends into the tip as an electrode for monopolar arcing within a lumen, the guide wire being highly flexible and having a radiopaque portion for simple identification of its location with x-ray apparatus.

According to one aspect of the invention, an electrosurgical apparatus for cutting tissue and for ablating occlusions includes means for selectively generating a train of relatively high energy and relatively low energy pulses of electrical energy for application to an electrically insulated wire having an attached electrode, the means for selectively generating having a variable output impedance, a load impedance comprising an impedance of the electrode, the wire, and their environs; means for sensing the load impedance relative to the output impedance in response to a train of low energy pulses applied to the wire and for adjusting the output impedance to match the load impedance in response to the sensed load impedance relative to the output impedance; and means for controlling the means for selectively generating and the means for sensing and adjusting to generate a train of low energy pulses and to match the output impedance to the load impedance and for subsequently generating a train of high energy pulses for producing an arc at the electrode.

In accordance with a second aspect of the invention, an electrosurgical apparatus for cutting tissue and for ablating occlusions includes means for generating a train of variable energy pulses of electrical energy for application to an electrically insulated wire having an attached electrode for producing an arc; means for measuring relative electrical energy produced by an arc at the electrode produced by a pulse; means for comparing the relative energy to a predetermined value to determine an energy difference; and means for adjusting the electrical energy of a subsequent pulse in response to the energy difference to reduce the energy difference for the subsequent pulse toward zero.

A guide wire according to the invention for supporting monopolar arcing comprises a flexible metal wire including a distal end, an electrically insulating coating extending along the wire, and an electrically and thermally insulating tip having a distal end and attached to the wire, the wire extending through the electrically insulating tip and forming an electrode at the distal ends of the wire and the electrically insulating tip.

BRIEF DESCRIPTION OF THE DRAWINGS

FIG. 4 is flow diagram illustrating a method of establishing an impedance match in an apparatus according to the invention.

DETAILED DESCRIPTION OF PREFERRED EMBODIMENTS

Figure 1:
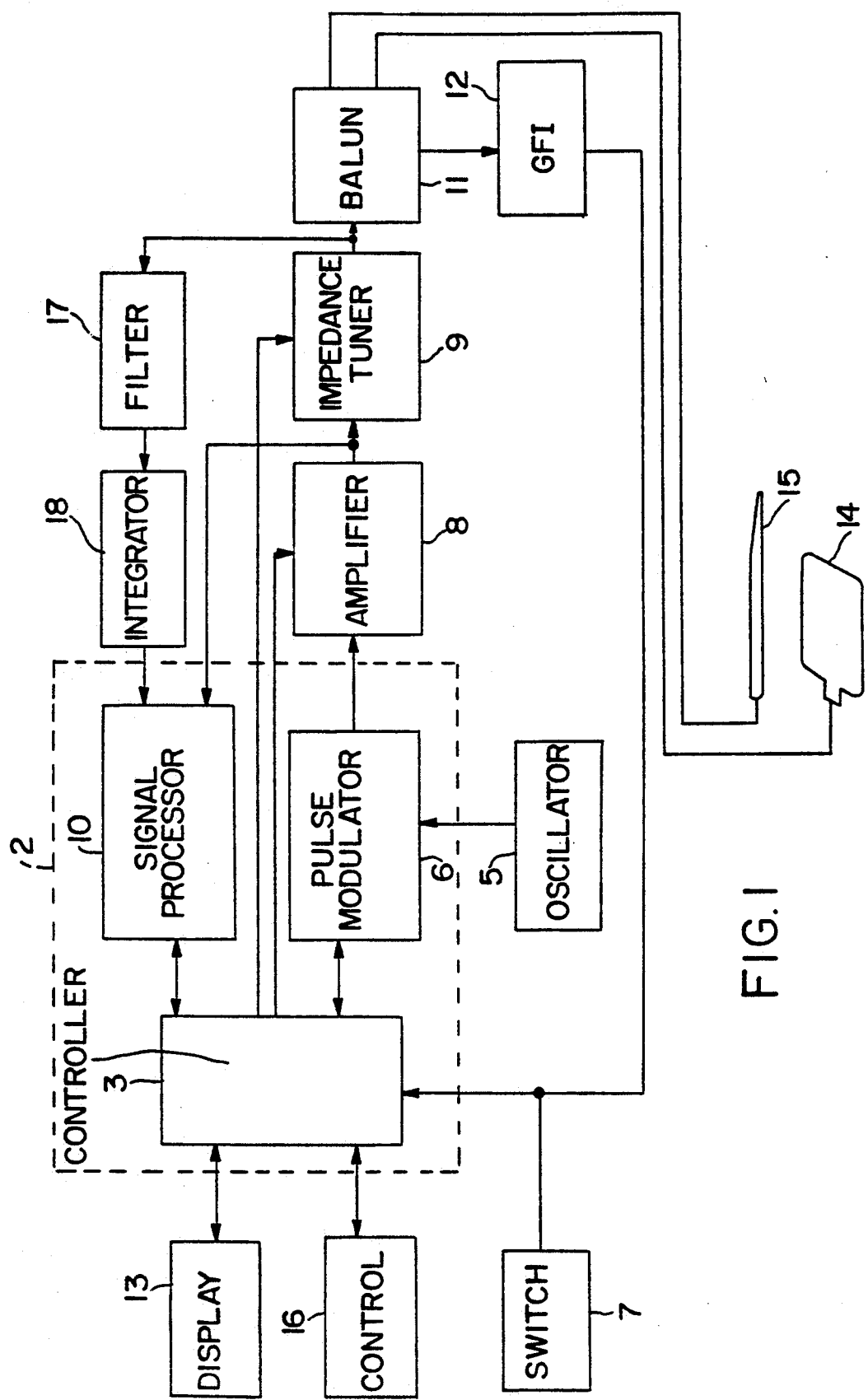
FIG. 1 is a block diagram of a vascular occlusion ablation apparatus according to an embodiment of the invention.

FIG. 1 is a schematic block diagram of an embodiment of an electrosurgical apparatus 1 according to the invention. The electrosurgical apparatus 1 includes a microprocessor 2 providing the control functions described below. The microprocessor 2 includes a controller 3 for controlling the input and output of information and instructions as well as controlling other parts of the microprocessor and the overall apparatus.

The apparatus generates pulses of electrical energy to produce arcing at an electrode to cut tissue and ablate an occlusion. The energy pulses are a modulated continuous wave signal. The continuous wave signal is generated by an oscillator 5. The oscillator 5 may be a conventional crystal controlled oscillator, such as a Colpitts oscillator. A preferred frequency of oscillation is 6.78 MHz. This frequency is allocated for medical uses and, through experimentation, it has been determined that it is more suitable for arcing ablation than are other frequencies that are allocated for medical applications and that have been traditionally used in electrosurgical equipment, such as the second and fourth harmonic of 6.78 MHz. The capacitive coupling between the wire with an attached electrode and the body of the animal being treated increases with frequency, making delivery of sufficient power for arcing to the wire increasingly difficult as frequency increases. However, at lower frequencies, the size of certain components increases, complicating construction and use of the apparatus. The preferred frequency reasonably limits the capacitive coupling and size of the apparatus.

The continuous wave signal generated by the oscillator 5 is supplied to a pulse modulator 6 that is part of the microprocessor 2. Preferably, the microprocessor 2 is an Intel 80386 or a similar type of microprocessor with which conventional disk operating software (DOS) can be employed so that the programming of the microprocessor can be easily carried out. In a preferred embodiment of the invention, the pulse modulator produces a train of twenty pulses each time the pulse modulator receives a "fire" signal from a switch 7. A typical pulse width is 200 microseconds and the pulses are typically spaced 2 milliseconds apart. A pulse shape that has been found to work well in electronic signal processing is a cosine squared shape. Accordingly, using conventional programming techniques, a train of cosine squared pulses is generated in the pulse modulator 6 and modulates the continuous wave signal.

It is known that there is sometimes a muscular reaction to the application of electrical pulses to tissues in animals. To reduce that twitching, the pulse modulator 6 also produces white noise that further modulates the cosine squared pulses. Thus, the pulse train which is supplied by the pulse modulator 6 to an amplifier 8 is a train of pulses, each pulse having a cosine squared shape modulated by white noise, and having a basic frequency of 6.78 MHz. The pulse modulation is thus carried out using software rather than hardware. The invention is not limited to the use of cosine squared pulses, and other waveforms, such as triangular and trapezoidal pulses, may be generated by the software and pulse modulator 6. Preferably, the pulse modulator 6 incorporates a watchdog timer that resets the entire microprocessor if a fault occurs in the execution of the modulation software. The watchdog timer "times out" and produces a reset signal if it does not receive a predetermined number of pulses within a predetermined time interval.

The amplifier 8 is capable of producing relatively high output energy, up to 2.5 kilowatts peak envelope power with an average power of 50 to 700 watts. The amplifier 8 also selectively produces a relatively low energy output for determining the impedance of the load and tuning the output impedance of the apparatus including an impedance tuner 9 described below.

Figure 2B:
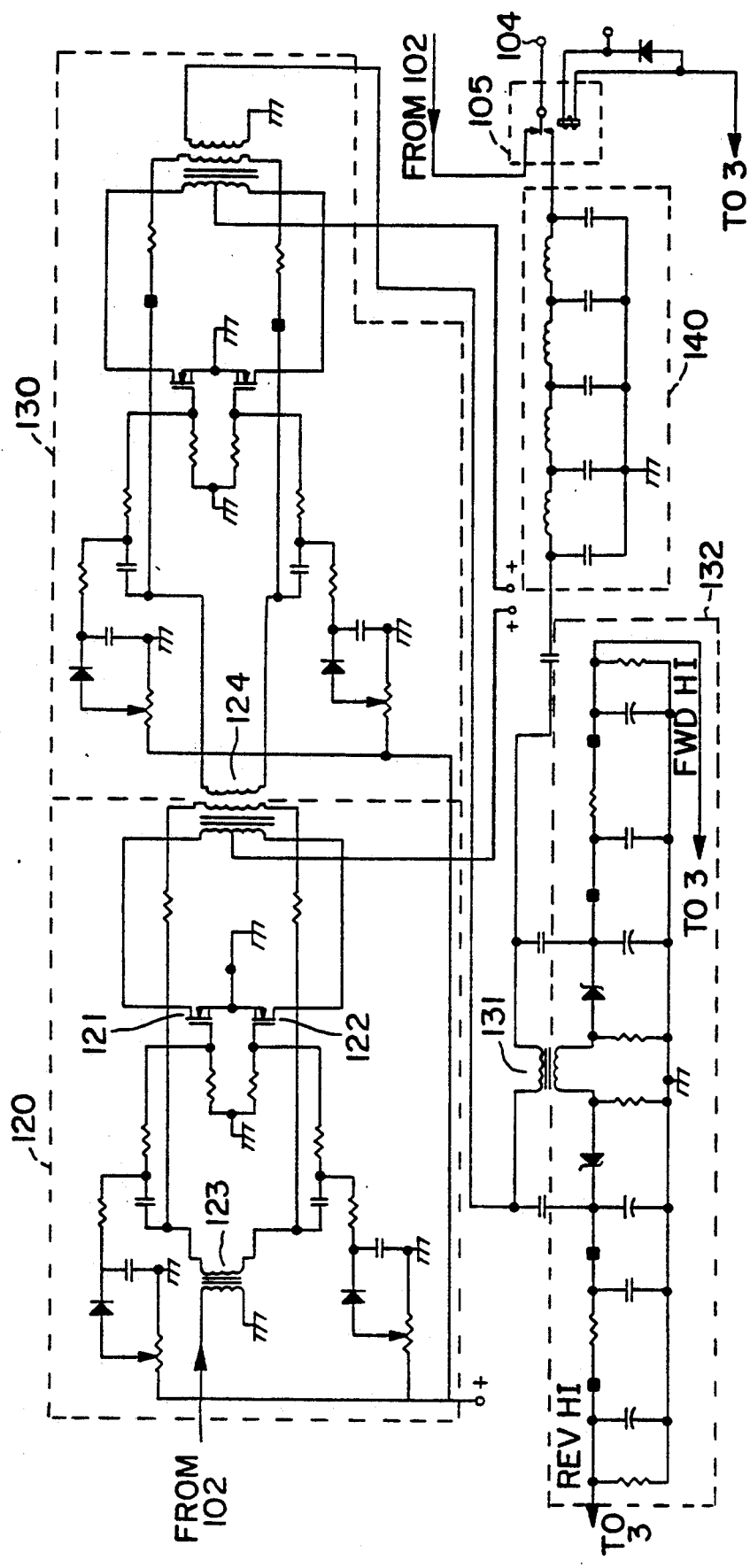
FIG. 2 is a schematic diagram of an embodiment of an amplifier that may be used in an apparatus according to the invention.

An embodiment of an amplifier 8 is shown in a schematic view in FIG. 2. Initially, the pulse train from the pulse modulator 6 is applied to a conventional preamplifier 101. The output signal from the preamplifier 101, referred to here as the low energy signal, is directly used in tuning the impedance tuner 9 as described below. When a relay 102 receiving the low energy signal is in the position indicated in FIG. 2 by the solid lines, the low energy signal is supplied to a conventional dual directional coupler 103. That coupler includes an input port for receiving the low energy signal and an output port connected to an amplifier output terminal 104 when a relay 105 is in the position indicated in FIG. 2. The dual directional coupler 103 samples the low energy signal from the preamplifier 101, i.e., the forward low energy signal, as well as the low energy signal reflected from the load, e.g., a wire within the lumen or an electrosurgical knife and their respective cables and environs, as described below. The reflected low energy signal enters the output port of the dual directional coupler 103 and is sampled. The sampled forward and reverse low energy signals pass through separate, identical circuits, respectively including impedance transformers 106 and 107, with respective resistive loads to match the impedance of the output ports of the directional coupler 103. The circuits respectively include diodes 108 and 109 for respectively detecting the envelopes of the low energy forward and reflected signals which, after passing through respective low pass filters, are passed to a signal processing section 10 of the microprocessor 2 for calculation of the ratio of the forward energy of the low energy signal to the reverse energy of the reflected low energy signal, i.e., the quality of the impedance match between the output impedance of the apparatus generating the pulse train and the load impedance of the wire and electrode within the lumen.

When the relay 102 is switched to the alternative position shown in FIG. 2, the low energy signal from the preamplifier 101 is passed to a driver circuit 120, another amplifier stage. The driver circuit 120 includes transistors 121 and 122 that are driven 180° out of phase by supplying the preamplified low energy signal through a transformer 123 to the two transistors. The resistors and capacitors otherwise shown as part of the driver circuit 120 in FIG. 2 are employed to supply appropriate bias voltages to the transistors. The driver circuit diodes are employed for temperature compensation. The out-of-phase signals produced by the transistors 121 and 122 are combined in a transformer 124, a matching transformer that transfers the amplified signal to a power amplifier 130. The transformer 124 is also used to supply a negative feedback signal to the driver circuit 120, improving the linearity of the gain of the driver circuit with respect to frequency.

The power amplifier 130 is fundamentally similar to the driver circuit 120. The high energy signal output from the power amplifier 130 is supplied, through the primary winding of a transformer 131, to a nine pole low pass filter 140 including five capacitors and four inductors to reduce the harmonic content of the high energy signal produced by the power amplifier 130. The high energy signal is supplied to the output terminal 104 when the relay 105 is switched to the alternative position shown in FIG. 2. A transformer 131 is part of a high power directional coupler 132. That coupler samples, through transformer 131, the forward energy, i.e., the high energy signal, of the amplifier 130 as well as the reflected energy, i.e., the high energy signal reflected from the load impedance, indicating an impedance mismatch. Those forward and reverse high energy signals may likewise be supplied to the signal processing section 10 of the microprocessor 2 shown in FIG. 1 for additional analysis of the quality of the match between the output impedance of the pulse source and the load impedance, if desired.

Returning to FIG. 1, the output signal, either the low energy signal or the high energy signal, is selectively supplied from the amplifier 8 in response to the controller 3 to the impedance tuner 9. The impedance tuner 9 provides a means for altering and improving the impedance match between the source impedance and the load impedance, improving the efficiency of energy transfer. The term "impedance match" as used here does not always mean an exact conjugate impedance match. Rather, as used here, the term "impedance match" means the closest possible matching of the output impedance of the pulse generating portion of the apparatus to the load impedance, for example, a cable, wire, electrode, lumen, and environs. That match may be an exact conjugate match but may also be a best available, non-conjugate impedance match that improves the efficiency of power transfer over that which could be achieved without the impedance tuner 9. An embodiment of the impedance tuner 9 is shown in FIG. 3.

Figure 3:
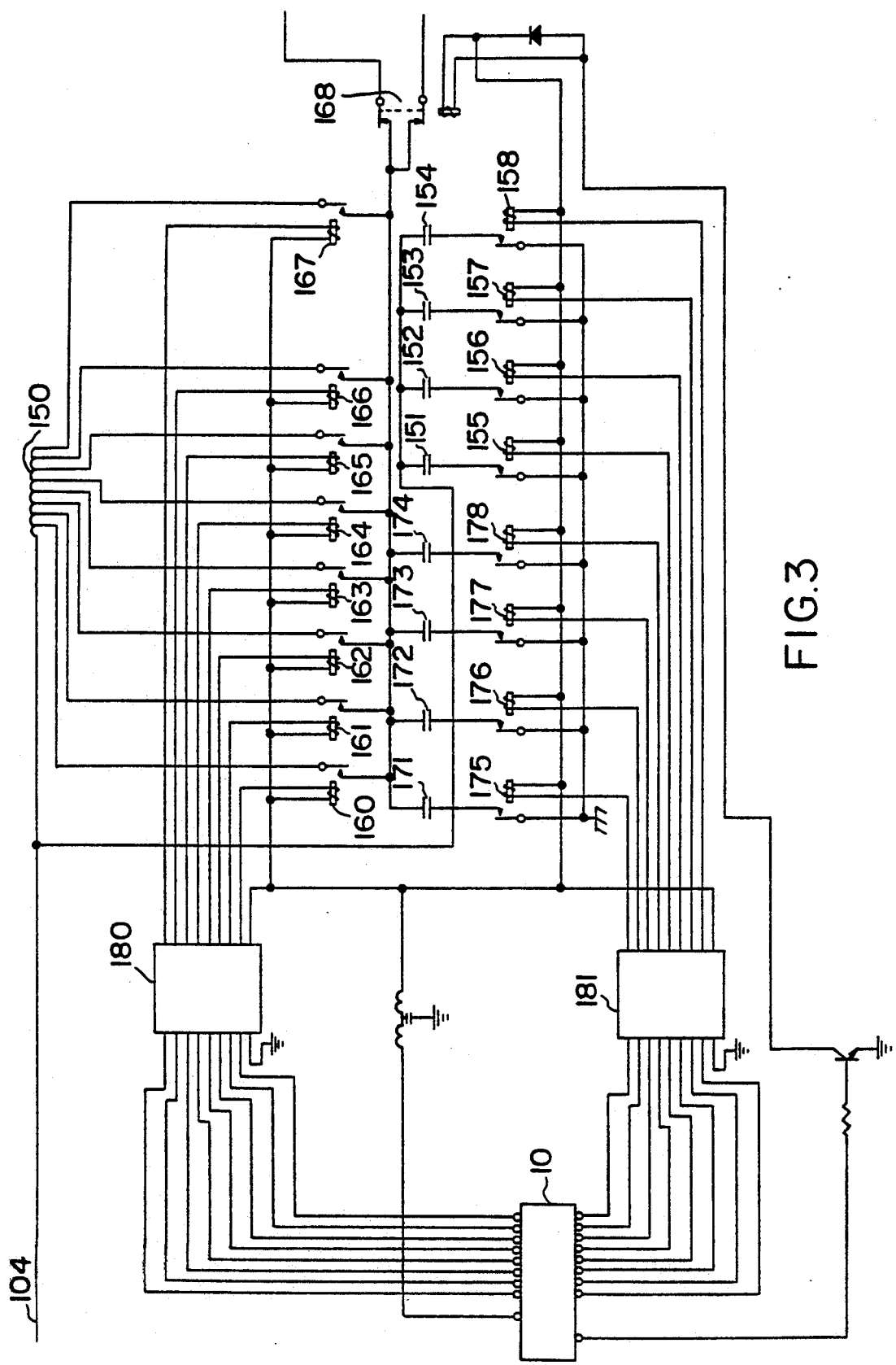
FIG. 3 is a schematic diagram of an embodiment of an impedance tuner that may be used in the invention.

In the impedance tuner of FIG. 3, the output signal, at either high or low energy, from the amplifier 8 is applied as an input signal to an autotransformer 150 that includes eight taps along its primary winding. The input side of that winding is also connected to each of four capacitors 151-154 which are respectively connectable to ground through respective relays 155-158. Similarly, each of the eight taps on the primary winding of the autotransformer 150 is connected through a respective relay 160-167 to an output line that is connectable through another relay 168 to the output terminal of the impedance tuner. The relay 168 determines whether the energy output from the impedance tuner is delivered to a dummy load or to a balun transformer that provides the connection to the load. Relay 168 is actuated by the controller 3 of the microprocessor 2. The output line of the impedance tuner is connected to each of four capacitors 171-174 which are respectively connectable to ground through relays 175-178.

The impedance tuner 9 enables the formation of a $\pi$ circuit including an inductor with capacitors connected to ground on either side of the inductor. The value of the inductor is determined by selecting one of the taps on the winding of the autotransformer by closing one of relays 160-167. The value of the capacitance at the input side of the inductor is determined by closing one or more of relays 155-158. None of those relays needs to be closed, all of those relays may be closed simultaneously, or one or more of those relays may be closed. Likewise, the value of the capacitor at the output side of the π circuit is chosen by closing combinations of relays 175-178. Again, none, all, or some of the relays 175-178 may be closed. The particular relays that are closed is determined by the controller 3 which supplies actuating signals to the relays through respective buffer circuits 180 and 181. The values of capacitors 151-154 (and 171-174) are chosen so that each successive capacitor is about one-half of the capacitance of the preceding capacitor and capacitances, excluding zero capacitance, extending by a factor of 15 from the lowest capacitance to the highest capacitance can be achieved by actuating various relays. The impedance tuner circuit 9 of FIG. 3 permits 2,048 different circuits to be connected from the switchably interconnectable capacitances and inductors.

An impedance tuner in accordance with the invention is not limited to the embodiment of FIG. 3. The number of connectable capacitors at the input and output sides of the inductor can be greater or fewer than four. The number of taps on the autotransformer may be greater or fewer than eight. A different circuit arrangement that is not a π filter may be employed with a plurality of switchably connectable reactive elements. The purpose of the tuner 9 is served by providing a number of reactive components, i.e., capacitors, inductors, or capacitive devices such as pin diodes, that may be selectively interconnected in order to provide a variety of circuits of different impedances for matching the output impedance of the source of energy pulses, including the tuner, to a load impedance. Examples of other elements that may be used as or in an impedance tuner include a tunable or adjustable inductor, capacitor, or transformer, for example, having a value selectable by electromechanical means, such as a motor.

A process for achieving the impedance match is illustrated in FIG. 4. As shown in FIG. 4, when the switch 7 is initially actuated at step 201, a determination is made in the microprocessor 2 as to whether the load impedance has not yet been matched to the output impedance. The controller 3 within the microprocessor 2 then controls the amplifier 8 to produce the low energy pulsed signal and to supply that low energy signal to the load through the impedance tuner 9. At step 202, the number of the n possible combinations of impedances in the impedance tuner 9, 2,048 combinations in the embodiment of FIG. 3, is set to zero. At step 203, the number of the combinations is incremented by one, initially to 1, so that the first of the possible circuitry combinations of the tuner 9 is selected from a list of all such combinations stored in a memory (not shown) within the controller 3 or outside but connected to the microprocessor 2 and communicating with the controller 3. At step 204, the forward low energy and reverse low energy signals are sampled by means of the dual directional coupler 103. Those sampled low energy signals are supplied in analog form to a signal processor 10 within the microprocessor 2. The signal processor 10 includes an analog-to-digital converter that converts the forward and reverse low energy signals to digital values and determines the ratio of forward to reverse energy. The ratio of the circuit combination under test is stored in the memory associated with the controller 3. At step 205, a test is made to determine whether all of the m impedance tuner combinations have been tested for the quality of the match. If not, steps 203-205 are repeated until all m combinations have been tested and the ratio of forward to reverse energy has been obtained for each combination. The highest ratio value indicates the best impedance match.

Once the ratios for all the combinations have been determined, in step 206, the maximum ratio is selected by the controller 3 and a test in step 207 is applied to determine whether an adequate impedance match can be achieved. A predetermined minimum acceptable forward-to-reverse energy ratio, such as 4, is specified in the controller 3. If that degree of matching cannot be achieved, then an error message is generated at step 208 and the apparatus is prevented from generating high energy pulses until corrective action is taken. Otherwise, at step 207, if adequate impedance matching can be achieved, the combination of reactive elements producing the highest forward-to-reverse energy ratio is connected in the impedance tuner 9 by the actuation of selected relays in response to signals supplied by the controller 3. The amplifier 8 is switched at step 209 to high energy output by actuation of the relays 102 and 105, and a high energy pulse train is supplied through the impedance tuner 9 to the wire in the lumen to produce an arc at an electrode adjacent an occlusion, as described below.

Preferably, after an initial impedance match is established with the impedance tuner 9, at step 210 the microprocessor 2 retains the combinations of relay closings, i.e., impedance matching circuits, that provide the best matches for a subset of the total possible circuit combinations, for example, for sixty-four combinations of relay closings of 2,048 possible combinations. In each subsequent actuation of the switch 7, the process flow passes from test 201 to step 211 so that only that subset of stored closest impedance matches, e.g., sixty-four combinations, is tested in step 211 to find the closest match rather than all possible impedance matching circuit combinations. Again, the closest match, i.e., the highest forward-to-reverse energy ratio, is selected at step 206. Generally, the pulse train is repeatedly applied to remove an occlusion. The impedance change after each arcing is relatively small. Thus, rather than enduring a delay of two to fifteen seconds while all combinations of circuitry available with the impedance tuner 9 are tested, a prompt impedance match is achieved after only a subset of all possible combinations is tested so that ablation can continue without undue delay. A shift in the best impedance match located centrally amongst the subset of ratios tested again is detected in step 212. In response to such a shift, entries within the subset of combinations are deleted while others are added in step 213 so that the selected impedance match remains near the midpoint of the subset. The changed subset is stored again at step 210. A large impedance change may occur in the course of an electrosurgical procedure, e.g., when the electrode is moved to a new position. If the best impedance match falls at one of the extremes of the subset, as determined at test 214, suggesting a large load impedance change, the process defaults to step 202 so that all possible impedance match combinations are again tested.

Figure 5:
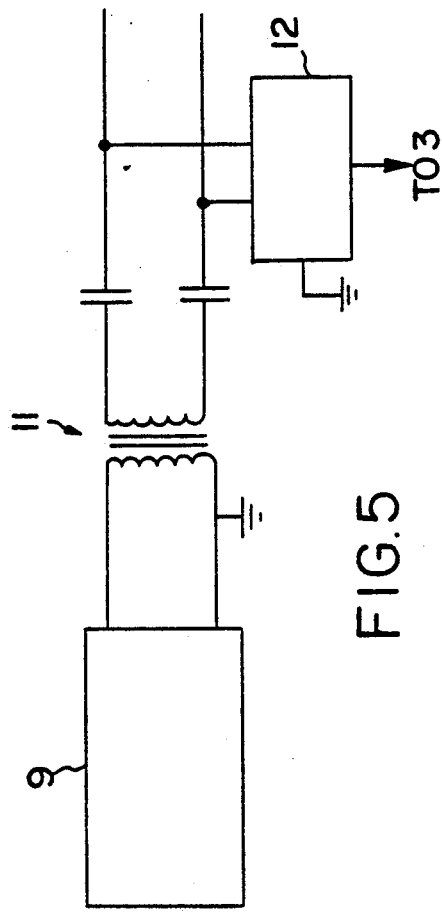
FIG. 5 is schematic diagram of a balun and ground fault interrupter that may be used in an embodiment of the invention.

FIG. 5 is schematic diagram of a balun and ground fault interrupter used in an embodiment of the apparatus in accordance with the invention. In FIG. 5, a balun 11, also shown in FIG. 1, is a transformer. That balun 11 provides radio frequency isolation from ground of the energy pulses as well as an impedance transformation between the output impedance and the load impedance. This transformation is encompassed in the impedance matching process described above. Capacitors are connected in each of the two leads of the secondary winding of the balun as high pass filters to attenuate low frequency signal components further. Those low frequency components can produce muscular reactions, i.e., twitching, in an animal being treated with the apparatus. Since the balun 11 provides a balanced output signal, it provides an opportunity to determine whether any ground fault exists within the apparatus or relative to other apparatus that may be connected to an animal being treated.

As shown in FIG. 5, a ground fault detector 12 is connected to the controller 3 of the microprocessor 2 for comparing the currents flowing in the two secondary leads of the balun. When, as intended, the output signal is balanced, i.e., equal currents flow in each of the secondary leads from the balun 11, no current will flow to ground when the signals on those lines are subtracted from each other. A comparison in the controller 3 of the currents in those two lines senses any current flow to ground that could result from an imbalance, indicating a possible interruption in a ground or a ground loop that might subject an animal being treated to risk of electrical shock. When a net current flows to ground, a signal is sent by the controller 3 to a display 13 which displays an error message and to the pulse modulator 6 to disable pulse generation until corrective action is taken.

The output leads of the balun are directly connected to the load. In one application of the apparatus, the load includes at least one wire inserted in a lumen and an electrode adjacent an occlusion where arcing takes place to remove the occlusion. The load may include a catheter for retrieving debris from the arcing, for infusing or extracting a fluid, and a second wire for bipolar arcing within the lumen. The load may include, as illustrated in FIG. 1, a single wire 15, sometimes called a guide wire, including an electrode at a distal tip for monopolar arcing in the lumen. In that case, the second lead of the balun 11 is connected to a dispersive electrode 14, sometimes called a ground pad, that is conventionally used in electrosurgery. That dispersive electrode is applied to a large area of the body of the subject being treated, usually in conjunction with a gel or other preparation to ensure good electrical contact between the dispersive electrode and the subject. The load may be a scalpel or other tissue cutting instrument that is used in conventional or percutaneous surgery. Of course, the load also includes the cable extending between the pulse generator and the wire, electrode, or scalpel where arcing occurs.

Figure 6:
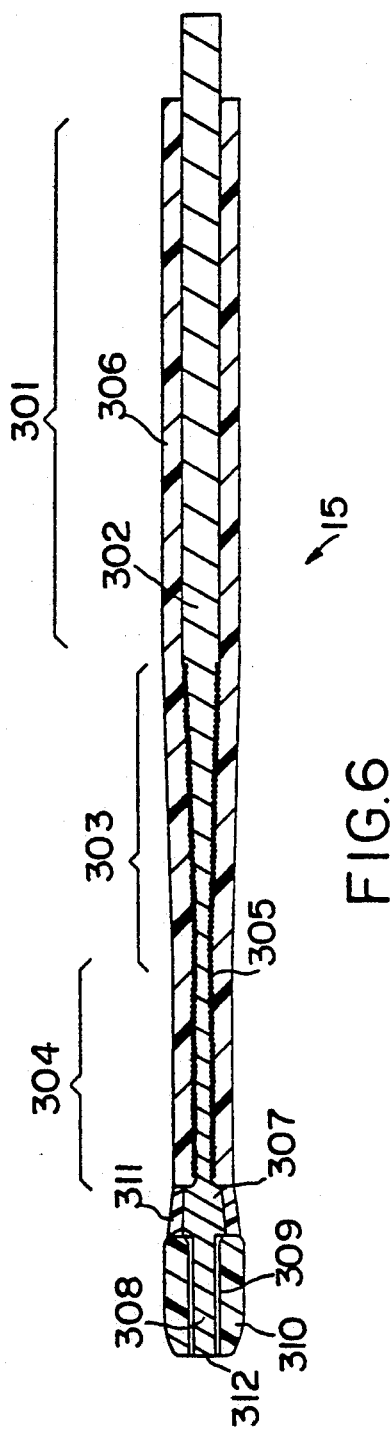
FIG. 6 is a sectional view of an embodiment of a guide wire according to the invention.

An embodiment of a guide wire 15 for monopolar arcing to ablate an occlusion and either vaporize plaque forming the occlusion or break plaque into such small particles that they do not adversely affect the circulatory system is shown in a cross-sectional view in FIG. 6. That embodiment includes several sections. The longest section, lead section 301, includes a flexible wire 302 of substantially uniform diameter. The wire 302 is a corrosion-resistant metal or alloy, such as stainless steel, titanium, nitinol, Elgiloy, Hastalloy, MP35N (a tradename of SPS Technologies), and the like, and has a length sufficient for the length of insertion of the guide wire 15 and connection to an external electrical lead that, in turn, is connected to the balun 11. Near the distal end of the guide wire, a tapered transition section 303 in which the diameter of the wire 302 gradually decreases toward the distal end joins the lead section 301. Still nearer the distal end, a reduced diameter section 304 of the wire 302, of a substantially uniform diameter, joins the transition section 303. The transition and reduced diameter sections 303 and 304 increase the flexibility of the guide wire 15. These transition and reduced diameter sections may be permanently bent into a curved or hook shape for particular applications, such as angioplasty.

A radiopaque wire 305 is wrapped in a coil around and transverse to the wire 302 along the transition and reduced diameter portions 303 and 304. The radiopaque wire may be any material that is easily identified in an x-ray and is available in a very small diameter, such as gold, platinum, iridium, or tungsten.

An electrically insulating coating 306, preferably a heat-shrinkable tubing, extends over the lead, transition, and reduced diameter sections 301, 303, and 304. The insulating coating 306 is a medically compatible electrical insulator, such as polyurethane, polyimide, polyethylene, and tetrafluoroethylene, commonly referred to as TEFLON, a trademark of E. I. duPont. TEFLON is a preferred material because it slides easily.

The wire 302 extends beyond the reduced diameter section 304 to a distal section 307 of essentially the same diameter as the wire 302 in the lead section 301 and to an end portion 308 of reduced diameter. The end portion 308 is received in a bore 309 of an electrically and thermally insulating tip 310. A film 312 is disposed within the bore 309 in contact with the internal surface of the bore 309 and the wire 302, forming part of the bond of the wire 302 to the tip 310. The distal end of the wire 302 is substantially flush with the distal end of the tip 310. The distal end of the wire 302, exposed at the distal end of the tip 310, forms an electrode for supporting a monopolar arc. The tip 310 electrically and thermally isolates the remainder of the guide wire from the arc. The distal end of the tip 310 preferably includes a blended series of radii to facilitate the insertion and advancement of the tip within a lumen or catheter.

The tip 310 may be alumina or another ceramic, glass, or even a high temperature polymer bead, so long as the tip material is not damaged by arcing at the electrode. The tip must have good thermal insulation characteristics to support arcing without damage to the wire 302 or the insulation coating the wire. When the tip 310 is ceramic, glass, or a similar material, the film 312 preferably includes a metallic film that is fired onto the internal surface of the bore 309 and a brazing composition that attaches the tip to the wire 302. Otherwise, the tip 310 is adhered to the wire 302 with a medically compatible bonding agent. The electrically insulating coating 306 does not extend to or cover the distal section 307 or reach the tip 310. Instead, a medical grade epoxy is applied to the distal section 307 as an insulating coating 311 between the proximal end of the tip 310 and the electrically insulating coating 306.

The guide wire 15 is not a catheter and does not include a lumen through which ablative debris can be extracted or through which fluid can be infused or withdrawn. However, the guide wire can be used in conjunction with a catheter, an endoscope, an angioscope, or other medical instruments within a body. In those applications, the guide wire is generally contained within and is inserted through the other instrument. In fact, the guide wire may be advanced in a lumen, organ, or body cavity in advance of the catheter, endoscope, or angioscope and function as a guide for the advancement of the other instrument.

The guide wire 15 is manufactured by grinding the tapered section 303, the reduced diameter section 304, the distal section 307, and the end portion 308 on the stainless steel wire 302. After attaching the tip 310 to the end portion 308, the radiopaque coil 305 is wound on the wire 302. Then, the insulating coating 306 is applied to the wire. Finally, the epoxy forming the insulating coating 311 is applied. The radiopaque coil permits the user of the guide wire to determine and follow its location within an animal being treated on an x-ray image but does not interfere with the flexibility of the transition section 303 of the wire 302.

The thickness of the insulating coating 306 and the diameter of the wire 302 strongly influence the impedance per unit length of the guide wire and its operation. In an embodiment of the guide wire that has worked well, the outside diameter of the insulating coating 306 was about 0.84 millimeter (0.033 inch). Generally, capacitance per unit length of the guide wire is inversely proportional to the logarithm of the outside diameter of the insulation, i.e., the insulation 306, to the diameter of the wire 302 within the insulation. If the capacitance per unit length of the guide wire is too high, too much power may be dissipated along the length of the wire to support an arc at the electrode at the end of the wire. For example, arcs were not supported by guide wires having an impedance per unit length of 500 pF/m but arcing was produced at an electrode at the end of a guide wire having an impedance per unit length of no more than 200 pF/m. Generally, any guide wire impedances per unit length of up to about 200 pF/m will support the desired arcing at an electrode at the end of the guide wire. This range of impedances per unit length of the guide wire also assists in designing the pulse generator since a range of guide wire impedances and matching output impedances can be established. Of course, regardless of other considerations, the insulation 306 must be sufficiently thick to protect a surgeon using the guide wire and the patient from electrical shock and sufficiently thin so that the insulated wire fits into small lumens.

In use, the guide wire 15 or another wire or a monopolar or bipolar catheter is inserted in an artery or vein and advanced to the location of the occlusion. The operator uses a control 16 for initiating operation of the apparatus in conjunction with the display 13, as shown in the block diagram of FIG. 1. The display 13 may be a multiple line cathode ray tube display or a liquid crystal display of a conventional type that is controlled by the controller 3 of the microprocessor 2 to display alphanumeric information. The control 16 may be a touch screen, a track ball, a joy stick, or another means of selecting options from a menu appearing on the display 13. Alternatively, the control 16 may be a simple push-button switch or key pad that prepares the apparatus for an arcing sequence. When the operator has placed the wire in a desired location and is prepared to begin arcing, the switch 7 is actuated. Typically, the switch 7 is a foot-operated switch, leaving the operator's hands free for controlling the positioning and advancing of the wire. Upon actuation of the switch, the apparatus produces a train of pulses incorporating the continuous wave signal from the oscillator 5 and the modulation of the pulse modulator 6 and passes the train of pulses to the amplifier 8. Through the controller 3, the amplifier 8 is controlled to generate the low energy signal which is supplied through the impedance tuner 9 and the balun 11 to the wire. At the direction of the controller 3, the impedance tuner 9 is tuned to the best impedance match between the output and load impedances provided that a certain minimum impedance match is achieved. Once the impedance match is achieved, the amplifier 8 is switched to the high energy signal and a train of pulses of electrical energy is supplied to the guide wire or catheter so that arcing takes place at the electrode. Preferably, only a single train of energy pulses is transmitted in response to each actuation of the switch 7. Upon the second and subsequent actuations of the switch 7, the impedance tuner 9 tests only a limited number of the total number of possible matching circuits to achieve the best impedance match whereupon the train of high energy electrical pulses is furnished by the amplifier 8 to the wire.

When tests are carried out using the guide wire 15 and a transparent phantom simulating an animal, the monopolar arc can be visually observed. At the same time, an acoustical signal resulting from the arcing occurring within a fluid can be heard. Likewise, an electrical response is produced by the arcing. When the apparatus is used within an animal, the arc usually cannot be seen or heard but the electrical response to the arcing can be detected as an indication of the quality of energy that is dissipated in the arc. The impedance tuning previously described ensures efficient energy transfer to the wire. By monitoring the electrical energy generated in response to the arc, the energy of the arc can be controlled, as necessary, to ensure that an adequate amount of energy is delivered in the arc to ablate an occlusion.

As shown in FIG. 1, in order to monitor the relative energy delivered to the arc, the electrical signal present on the wire as a consequence of the arcing is monitored by the signal processor 10 through a filter 17 and an integrator 18. The filter 17 is connected at a point of constant impedance within the apparatus, for example, between the impedance tuner 9 and the balun 11.

Figure 7:
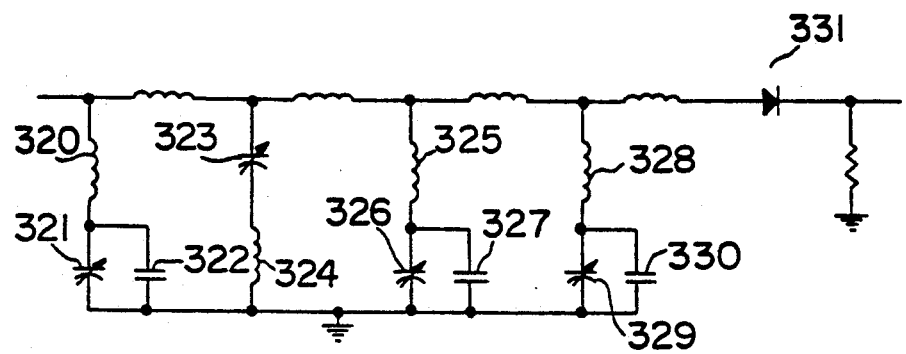
FIG. 7 is a schematic diagram of a filter for monitoring pulse energy that may be used in an apparatus according to an embodiment of the invention.

Since the sampling point is subjected to both the relatively high energy signal supplied to the wire as well as a relatively weak signal propagating on the wire as a result of the arc during the energy pulse producing the arc, a low pass notch filter is employed to reject the fundamental and harmonic frequencies of the driving high energy signal. An example of such a filter is illustrated in FIG. 7. The filter includes a first filter section comprising an inductor 320 connected in series with two parallel-connected capacitors 321 and 322 that are connected to ground. The capacitor 321 is a variable capacitor so that the resonant frequency of the first filter section can be tuned to the fundamental frequency of the pulsed signal. The second section of the filter, connected through an inductor to the first section, includes a series-connected variable capacitor 323 and an inductor 324 that are connected to ground. These two reactive components are tuned to the second harmonic of the pulsed signal supplied to the wire. Third and fourth filter sections, similar to the first filter section, are serially connected to the second filter section through respective inductors. The third filter section includes an inductor 325 connected in series to parallel-connected capacitors 326 and 327, capacitor 326 being variable in capacitance. The fourth filter section includes inductor 328 connected in series with parallel-connected capacitors 329 and 330, capacitor 329 being a variable capacitance element. The four filter sections provide a bandwidth sufficiently wide to attenuate the fundamental and second harmonic frequency as well as the side lobes of the pulsed energy. The resultant signal, so filtered, is rectified by a diode 331 and supplied to the signal processor 10 through an integrator 18.

Figure 8:
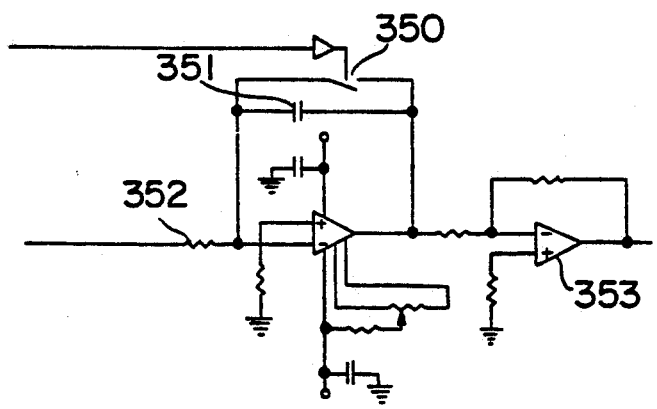
FIG. 8 is a schematic diagram of an integrator that may be employed in an embodiment of an apparatus according to the invention.

An example of an embodiment of the integrator 18 is shown in FIG. 8. The integrator of FIG. 8 is connected to the filter of FIG. 7 through a coaxial cable which functions as an additional low pass filtering section. The integrator is conventional. An analog switch 350 is connected in the feedback path of an operational amplifier in parallel with the integrating capacitor 351. The integration constant of the integrator is determined by the values of the input resistor 352 and the capacitor 351. The switch 350, which responds to a signal from the controller 3, is normally closed. At the beginning of each pulse, the switch 350 is opened so that integration may take place and capacitor 351 may be charged by the filtered signal applied to the input of the integrator. The integrator provides an output signal that is an analog representation of the sum of the electrical signals produced by the arc at the electrode at the end of the wire, i.e., the relative energy produced in the arc. This signal is passed through an amplifier 353 which increases the amplitude of the sum. At the conclusion of the pulse, switch 350 is closed so that the capacitor 351 is discharged and prepared for the next pulse. In the meantime, the output signal from the integrator 18 is supplied to the signal processor 10 where, preferably, the signal is converted to a digital form in an analog-to-digital converter. That digital value is compared to a predetermined threshold value, which represents a relative energy that it is desired to deliver in the arc, in the controller 3. With the preferred pulse width and pulse interval, it is possible to measure the relative energy delivered in one pulse within a train of pulses and to make an adjustment of the gain of the amplifier 8 before the generation of the next pulse so that pulse-to-pulse adjustments can be made in the energy delivered in the arc during a single pulse train. The pulse energy may also be adjusted without altering pulse amplitude, i.e., the gain of the amplifier, since the total energy delivered in a pulse also depends on pulse width. In other words, pulse width, pulse position, and other pulse parameters may be changed to adjust the pulse energy toward a desired value.

Although not illustrated in any of the figures, a power supply is required to supply the appropriate voltages and currents to the apparatus shown in FIG. 1. The power supply may be conventional although, because the power output of the apparatus is relatively high, requiring moderate power consumption, the power supply preferably includes means for efficient power consumption. For example, the primary transformer in the power supply may be a ferroresonant transformer having a capacitor connected to one of the windings for resonance at the line frequency.

As described, the invention includes several particularly important features. The apparatus includes a unique, highly flexible, electrically insulated guide wire with an electrically and thermally insulating tip that is easily advanced through a lumen, such as an artery or vessel, and that is easily identified in position because of its radiopaque winding adjacent the tip. The electrical energy source includes means for automatically matching its output impedance to the load impedance presented by a wire with an attached electrode, the lumen in which the wire or catheter is disposed, and the environs, such as the liquid filling the lumen. The automatic impedance matching compensates for the changing load impedance conditions in the lumen and as the wire or catheter is advanced within the lumen, ensuring that efficient power transfer to the electrode takes place so that the desired ablation of an occlusion is achieved. The energy supplied to the ablating arc in each pulse is continually monitored to determine whether the desired level of energy is supplied by the arc in each pulse. Adjustments in the energy of pulses within a pulse train of electrical energy pulses is made by a means for measuring the relative energy of the arc, comparing that relative energy to a predetermined value, and adjusting the gain of an amplifier from which the pulses are supplied.

The invention has been described with respect to certain preferred embodiments. Various additions and modifications within the spirit of the invention will occur to those of skill in the art from the foregoing description. Accordingly, the scope of the invention is limited solely by the following claims.

We claim:

1. An electrosurgical apparatus for cutting tissue and for ablating occlusions comprising:
    means for selectively generating a train of relatively high energy pulses and a train of relatively low energy pulses of electrical energy for application to a wire having an attached electrode, the means for selectively generating having a variable output impedance, a load impedance of the means for selectively generating comprising an impedance of the wire having an attached electrode;
    means for sensing the load impedance relative to the output impedance in response to the train of low energy pulses applied to the wire and for adjusting the output impedance to match the load impedance in response to the sensed load impedance relative to the output impedance; and
    means for controlling the means for selectively generating and the means for sensing and for adjusting to generate the train of low energy pulses and to match the output impedance to the load impedance and for subsequently generating the train of high energy pulses for producing an arc at the electrode to ablate an occlusion.

2. The apparatus of claim 1 wherein the means for selectively generating comprises an oscillator for producing a continuous wave signal, a pulse modulator connected to the oscillator for forming pulses of the continuous wave signal, and an amplifier connected to the pulse modulator for amplifying the pulses of the continuous wave signal and producing the trains of relatively low energy and relatively high energy pulses of electrical energy.

3. The apparatus of claim 2 wherein the amplifier includes a preamplifier initially amplifying the pulses of the continuous wave signal and producing the train of relatively low energy pulses and a power amplifier for receiving and amplifying the train of relatively low energy pulses and producing the train of relatively high energy pulses.

4. The apparatus of claim 1 wherein the means for sensing and adjusting comprises a directional coupler for monitoring the relatively low energy pulses delivered to the load impedance to determine a forward energy and the relatively low energy pulses reflected from the load impedance to determine a reflected energy for comparing the forward energy to the reflected energy.

5. The apparatus of claim 1 wherein the means for sensing and adjusting comprises a plurality of reactive electrical components switchably interconnectable with each other and connected between the amplifier and the output impedance for interconnection in response to the means for controlling to match the output impedance to the load impedance.

6. The apparatus of claim 5 wherein the reactive components comprise a transformer including a winding having a plurality of taps and a plurality of capacitors connectable to the taps and to the winding for producing a plurality of impedances for matching the output impedance to the load impedance.

7. The apparatus of claim 1 wherein the means for controlling comprises a microprocessor.

8. The apparatus of claim 7 including a visual display connected to the microprocessor.

9. The apparatus of claim 1 including a switch for actuating the means for selectively generating wherein, each time the switch is actuated, the train of relatively low energy pulses is generated, the means for sensing and adjusting matches the output impedance to the load impedance using the relatively low energy train of pulses, and the train of relatively high energy pulses is generated after the output impedance is matched to the input impedance to ablate the occlusion.

10. The apparatus of claim 1 including a balun transformer coupling the means for sensing and adjusting to the load impedance.

11. The apparatus of claim 10 wherein the balun transformer includes two leads and including ground fault interrupting means connected to the balun transformer for disabling the means for selectively generating when current flow through the two leads of the balun transformer is unbalanced.

12. The apparatus of claim 1 including means for measuring relative electrical energy produced by the arc at the electrode by a relatively high energy pulse of the train of relatively high energy pulses, means for comparing the relative electrical energy to a predetermined value to determine an energy difference, and means for adjusting the electrical energy of a subsequent pulse in response to the energy difference to reduce the energy difference for the subsequent pulse toward zero.

13. The apparatus of claim 12 wherein the means for measuring includes a filter for rejecting a primary frequency and at least one harmonic frequency of the trains of relatively high energy and relatively low energy pulses.

14. The apparatus of claim 13 wherein the means for measuring includes an integrator connected to and receiving signals from the filter.

15. The apparatus of claim 12 wherein the means for comparing includes an analog-to-digital converter for converting the relative electrical energy into a digital value for comparison with the predetermined value.

16. The apparatus of claim 12 wherein the means for selectively generating comprises an oscillator for producing a continuous wave signal, a pulse modulator connected to the oscillator for forming pulses of the continuous wave signal, and a variable gain amplifier connected to the pulse modulator for amplifying the pulses and producing the trains of relatively high energy and relatively low energy pulses of electrical energy.

17. An electrosurgical apparatus for cutting tissue and for ablating occlusions comprising:
    means for generating a train of variable energy pulses of electrical energy for application to a wire connected to an output terminal of the means for generating and having an electrode attached to the wire for producing an arc in response to the pulses of electrical energy;
    means for measuring relative electrical energy produced by the arc at the electrode produced by a pulse including a filter connected to the output terminal in parallel with the wire and the attached electrode for rejecting a primary frequency and at least one harmonic frequency of the train of variable energy pulses of electrical energy;
    means for comparing the relative electrical energy produced by the arc to a predetermined value to determine an energy difference; and
    means for adjusting the electrical energy of a subsequent pulse in response to the energy difference to reduce the energy difference for the subsequent pulse toward zero.

18. The apparatus of claim 17 wherein the means for measuring the electrical energy includes an integrator.

19. The apparatus of claim 17 wherein the means for comparing includes an analog-to-digital converter for converting the relative electrical energy produced by the arc into a digital value for comparison with the predetermined value.

20. The apparatus of claim 17 wherein the means for generating comprises an oscillator for producing a continuous wave signal, a pulse modulator connected to the oscillator for forming pulses of the continuous wave signal, and a variable gain amplifier connected to the pulse modulator for amplifying the pulses and producing the train of variable energy pulses of electrical energy.

21. The apparatus of claim 17 including control means for controlling the means for generating and the means for adjusting, the control means comprising a microprocessor.

22. The apparatus of claim 21 including a visual display connected to the microprocessor.

* * * * *